United States Patent [19]

Yalamanchili

[11] Patent Number: 4,962,199

[45] Date of Patent: Oct. 9, 1990

[54] PYRIDAZINES BY MAGNESIUM HALIDE CATALYZED CYCLIZATION

[75] Inventor: Gopi Yalamanchili, St. Louis, Mo.

[73] Assignee: Monsanto Company, St. Louis, Mo.

[21] Appl. No.: 473,140

[22] Filed: Feb. 1, 1990

Related U.S. Application Data

[63] Continuation of Ser. No. 334,030, Apr. 6, 1989, abandoned.

[51] Int. Cl.$^5$ .......................................... C07D 237/02
[52] U.S. Cl. ................................................... 544/239
[58] Field of Search ......................................... 544/239

[56] References Cited

U.S. PATENT DOCUMENTS

| | | | |
|---|---|---|---|
| 4,661,145 | 4/1987 | Fujimoto | 544/239 |
| 4,707,181 | 11/1987 | Fujimoto | 71/92 |
| 4,732,603 | 3/1988 | Patterson | 544/239 |

*Primary Examiner*—Donald G. Daus
*Attorney, Agent, or Firm*—Stanley M. Tarter; George R. Beck; Howard C. Stanley

[57] ABSTRACT

The present invention relates to a process for making substituted 4-oxo-1,4-dihydropyridazines by reacting a 2-phenylhyrazono-3-oxoglutarate with an organic acid halide in the presence of magnesium halide.

10 Claims, No Drawings

PYRIDAZINES BY MAGNESIUM HALIDE CATALYZED CYCLIZATION

This is a continuation of application Ser. No. 334,030, filed on Apr. 6, 1989, now abandoned.

FIELD OF THE INVENTION

The present invention relates to a process for making substituted 4-oxo-1,4-dihydropyridazines.

BACKGROUND OF THE INVENTION

Certain carboxy substituted 4-oxo-1,4-dihydropyridazines and carboalkoxy substituted 4-oxo-1,4-dihydropyridazines are known in the art to have plant gametocidal activity as disclosed in U.S. Pat. Nos. 4,707,181 issued on Aug. 24, 1982 to T. T. Fujimoto and 4,732,603 issued on Mar. 22, 1988 to D. R. Patterson. These patents disclose preparing these compounds by reacting a 2-phenylhydrazono-3-oxoglutarate with an organic acid chloride in the presence of a Grignard reagent (isopropyl magnesium chloride). This process resulted in low yields of product and involved the use of the reactive and expensive Grignard reagent. There still is a need in the art for a more efficient and commercially viable process for making substituted 4-oxo-1,4-dihydropyridazines.

SUMMARY OF THE INVENTION

The present invention relates to a process for making substituted 3,5-bis(carboalkoxy)-4-oxo-1-phenyl-1,4-dihydropyridazines by reacting a substituted 2-phenylhydrazono-3-oxoglutarate with an organic acid halide in the presence of a base and magnesium chloride, magnesium bromide or magnesium iodide.

The process of the present invention results in high yield of the product 3,5-bis(carboalkoxy)-4-oxo-1,4-dihydropyridazines without the use of Grignard reagent. Other advantages of the process of the present invention will become apparent from the detailed description which follows.

DETAILED DESCRIPTION

The present invention relates to a process for making a compound of Formula I:

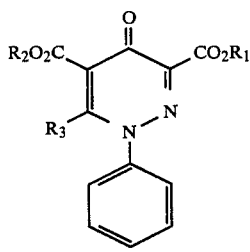

Formula I wherein $R_1$ and $R_2$ are each independently lower alkyl; and $R_3$ is lower alkyl, benzyl or phenyl; which comprises reacting a compound of Formula II:

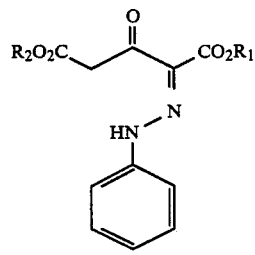

Formula II with $R_3COA$ wherein A is halo, in the presence of a base and at least about 0.25 molar equivalents of $MgX_2$, wherein X is Cl, Br or I, per mole of the compound of Formula II and wherein the phenyl ring of the compound of Formula II can be unsubstituted or substituted with one to three substituents which do not unacceptably interfere with the process.

A preferred embodiment of the process of the present invention provides a compound of Formula III:

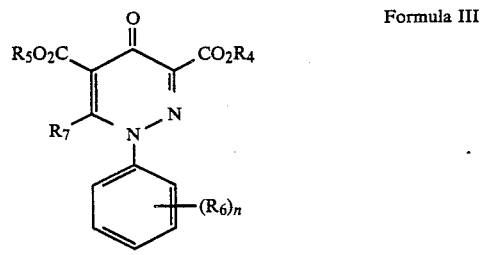

Formula III wherein $R_4$ and $R_5$ are each independently a lower alkyl, $R_6$ is halo; $R_7$ is lower alkyl and n is an integer from 1 to 3; which comprises reacting a compound of Formula IV:

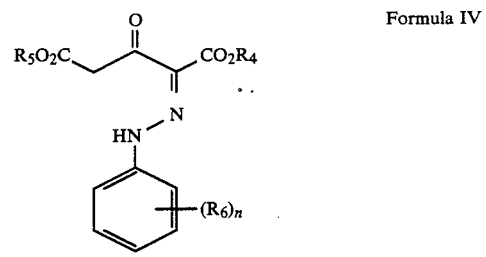

Formula IV with $R_7COA$ wherein A is halo, in the presence of at least about 0.25 molar equivalents of $MgCl_2$ per mole of the compound of Formula IV and an organic base. Preferably, A is chloro, n is 1 and $R_6$ is chloro, preferably para-chloro.

Another embodiment of the process of the present invention provides a compound of Formula V:

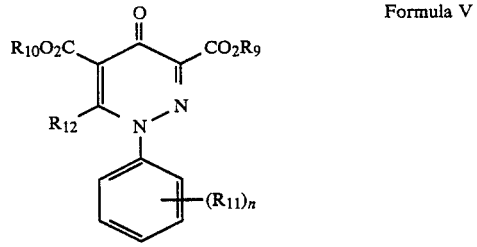

Formula V wherein $R_9$ and $R_{10}$ are each independently lower alkyl; each $R_{11}$ is independently halo, nitro, halomethyl, lower alkyl, lower alkoxy or cyano; $R_{12}$ is lower alkyl, benzyl or phenyl unsubstituted or substituted with up to three substituents each independently halo, nitro, halomethyl, lower alkoxy or cyano and n is 0 or an integer from 1 to 3; which comprises reacting a compound of Formula VI:

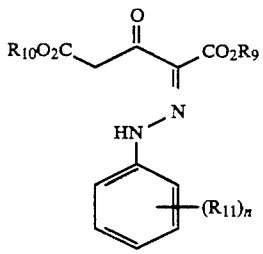

Formula VI with $R_{12}COA$ wherein A is halo, in the presence of a base and at least about 0.25 molar equivalents of $MgX_2$, wherein X is Cl, Br or I, per mole of the compound of Formula VI.

The term "lower alkyl" is intended to mean a straight-chain, branched-chain or cyclic akyl radical having from 1 to about 5 carbon atoms.

The term "halo" is intended to mean fluoro, chloro, bromo or iodo.

In the process of the present invention, the starting 2-phenylhydrazono-3-oxoglutarate is conveniently mixed together in a suitable solvent with a base and at least about 0.25 molar equivalents of magnesium salt per mole of the 3-oxoglutarate. It is believed that a magnesium complex of the 3-oxoglutarate is formed in this mixture. To the mixture is added an organic acid halide to form the 4-oxo-1,4-dihydropyridazine product.

The starting 2-phenylhydrazono-3-oxoglutarate can be conveniently made by reacting 3-oxoglutarate with a benzenediazonium chloride generally in accordance with known procedures such as those disclosed in the above-referenced U.S. patents.

The section of organic acid halide for use in the process of the present invention will be dependent on the nature of the substituent desired in the 6-position of the product 4-oxo-1,4-dihydropyridazine. Preferably organic acid chlorides are utilized. Suitable organic acid chlorides include both alkyl and aryl acid chlorides such as acetyl chloride, propionylchloride, butyryl chloride, valeryl chloride, benzoylchloride and the like. Those skilled in the art will be able to select other suitable organic acid halides for use in the process of the present invention.

Generally the oxoglutarate starting material is reacted with an excess of the organic acid halide, preferably an excess such as from about 1.05 molar equivalents up to about 2 molar equivalents or more of the organic acid halide for each mole of the 3-oxoglutarate. In the process of the present invention, the alkyl and aryl substituents on the 3-oxoglutarate and the organic acid halide reactants can be in turn substituted by one or more of a variety of other substituents which do not unacceptably inhibit or interfere with the process of the present invention and do not unacceptably interact with the solvents or reactants employed in the process such as halo, nitro, halomethyl, lower alkoxy and cyano. Processes using reactants having such substituents are contemplated as equivalents of the claimed process.

The magnesium salt is selected from magnesium chloride, magnesium bromide, magnesium iodide and mixtures thereof, and is preferably magnesium chloride. In the process of the present invention at least about 0.25 molar equivalent of the magnesium salt, preferably greater than about 0.50 molar equivalents of the salt and more preferably about 0.75 to about 1.0 molar equivalents of the salt for each mole of starting 2-phenylhydrazono-3-oxoglutarate is utilized. It is believed that the cation of the magnesium salt complexes with the starting 3-oxoglutarate to facilitate the reaction. Those skilled in the art will appreciate that other types of magnesium salts which will complex with the starting 3-oxoglutarate can be utilized in the process of the present invention and processes using such magnesium salts are contemplated as equivalents of the claimed process. Polymeric magnesium salts such as $MgF_2$ and $MgSO_4$ are not suitable for use in the process of the present invention.

Suitable bases for the process of the present invention include both organic and inorganic bases. It is believed that the base functions to deprotonate the 3-oxoglutarate during the reaction. Suitable inorganic bases include Group I and II metal hydrides such as sodium hydride and the like. Suitable organic bases include both alkyl and aromatic bases such as alkyl, cycloalkyl, and aryl amines, metallic amides and aromatic amines. Suitable alkyl and aryl amines include diethylamine, triethylamine, benzylamine, piperidine, piperazine, pyrrolidine, and the like. Alkylamines, such as triethylamines, are preferred. Suitable metallic amides include sodium amide and lithium diisopropyl amide. Suitable aromatic amines (aromatic, nitrogen heterocylic compounds) include imidazole, pyrazole, pyridine, pyrimidine, pyridazine and the like. Those skilled in the art will appreciate that other bases can be utilized in the process of the present invention. A sufficient amount of base is added to the reaction mixture to enable the reaction to proceed. Conveniently the amount of base added will be from about 1.0 to about 1.25 molar equivalents of base per mole of 3-oxoglutarate starting material. An excessive amount of base may hinder formation of the product.

The process is conveniently run in a nonprotic, inert solvent, preferably an organic solvent. Suitable organic solvents for the process of the present invention include such solvents as tetrahydrofuran, toluene, xylene, dichloromethane and ethyl acetate.

In the process of the present invention, the oxoglutarate starting material is conveniently stirred with the magnesium salt and an organic base in a suitable organic solvent and heated to an elevated temperature of from about 30° C. to the boiling point of the solvent, preferably from about 30° C. to about 110° C., to disperse the reactants throughout the solvent. Typically, the mixture is then cooled to a temperature below the boiling point of the acid halide. Typically, for acid chloride reactants, the temperature of the mixture is cooled from about 30° C. to about 60° C. The organic acid chloride is added with stirring. Preferably, the mixture is then stirred for a short period of time up to about 1 hour. The mixture is then cooled to room temperature and the product 4-oxo-1,4-dihydropyridazine isolated by standard laboratory procedures (e.g. by extraction and recrystallization).

The carboalkoxy substituted 4-oxo-1,4-dihydropyridazines made by the claimed process have gametocidal activity as disclosed in the above-referred U.S. Pat. No. 4,707,181.

The following examples are presented to illustrate various embodiments of the invention. These examples are illustrative of the novel process of the invention and do not imply any limitations to its scope.

EXAMPLE 1

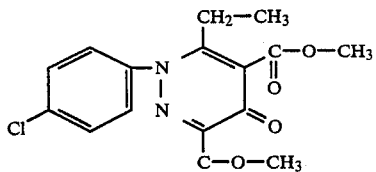

6-ethyl-3,5-bis(methoxycarbonyl)-4-oxo-1-(4-chlorophenyl) 1,4-dihydropyridazine.

A mixture of 1.25 g (4 mmol) of dimethyl 3-oxy-2 (4-chlorophenylhydrazono)glutarate, 0.404 g (4 mmol) of triethylamine; 0.38 g (4 mmol) of $MgCl_2$ (1 molar equivalent) in 15 ml of THF was heated to reflux for about 30 minutes. The mixture was then cooled to about 30° C. and 0.74 g (8 mmol) of propionyl chloride was added with stirring. The mixture was heated to 55° C. and stirred for about ½ hour. The mixture was then cooled to room temperature and mixed with 30 ml of ethyl acetate and 15 ml of 1 N HCl and stirred for 5 minutes to extract the desired product into the organic layer. The ethyl acetate extract was analyzed by gas chromatography. The yield of the desired product was determined by calculating the gas chromatograph (G.C.) area percent and was about 90% yield.

Following the procedure set forth above but varying only the amount of $MgCl_2$ in the reaction mixture, the following results were obtained.

| | mmol of $MgCl_2$ per mmol of glutarate | Product Yield by G. C. (Area %) |
|---|---|---|
| 1. | 0.75 | 90% |
| 2. | 0.50 | 86% |
| 3. | 0.25 | 64% |

EXAMPLE 2

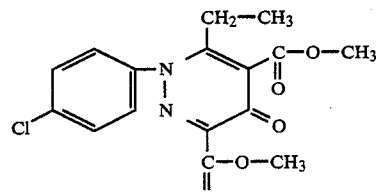

6-ethyl-3,5-bis(methoxycarbonyl)-4-oxo-1-(4-chlorophenyl)-1,4-dihydropyridazine.

A mixture of 10.06 g (32 mmol) of dimethyl-3-oxo-2(4-chlorophenylhydrazono)glutarate, 4.6 ml (33 mmol) of triethylamine, 3.04 g (32 mmol) of anhydrous magnesium chloride in 150 ml of THF was heated at reflux (~66° C.) for 30 minutes. The mixture was cooled to 20° C., 5.65 ml (65 mmol) of propionyl chloride was added and the mixture stirred for 5 minutes. The temperature was raised to 50° C. and the mixture stirred for 30 minutes. The mixture was cooled to 40° C. and about 80% of the THF was distilled out. The residue was mixed with 100 ml of toluene and 50 ml of 1N HCl and stirred for 5 minutes to extract the desired product into the organic layer. To determine the yield of the desired product, the product was hydrolyzed to the corresponding 3,5-bis(carboxy) compound. The organic layer was washed with water, concentrated to about 30 ml and treated with 60 ml of 10% sodium hydroxide. The mixture was stirred with additional water at 55° to 60° C. for 2.5 hours under vacuum to remove the toluene and water azeotrope. The solution was cooled to 15° C., acidified with 9.5 ml of conc. sulfuric acid, filtered and washed with water. The wet cake was mixed with 70 ml of methanol, stirred at 55° C. for 10 minutes, cooled to 20° C., filtered and air dried to give 8.57 g of a yellow colored solid product m.p. 233°–34° C. (decomposes) with a yield of ~82% determined by standard weight percent analysis method using HPLC.

EXAMPLE 3

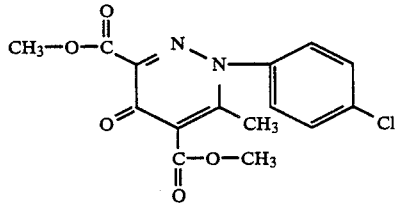

6-methyl-3,5-bis(methoxycarbonyl)-4-oxo-(4-chlorophenyl)-1,4 dihydropyridazine.

A mixture of 1.25 g (4 mmol) of dimethyl 3-oxo-2(4-chlorophenylhydrazono)glutarate, 0.404 g (4 mmol) of triethylamine, 0.380 g (4 mmol) of anhydrous $MgCl_2$ in 15 ml of THF was heated at reflux for 30 minutes. The mixture was cooled to 40° C. and treated with 0.628 g (8 mmol) of acetyl chloride. The mixture was then heated to 50°–55° C. and stirred for 30 minutes. The mixture was then cooled to room temperature and treated with 30 ml of ethyl acetate and 15 ml of 1 N HCl. The ethyl acetate layer was washed with water and the solvent evaporated. The residue was recrystallized from toluene/hexane to give 850 mg of a yellow solid product, m.p. 156°–158° C. (Yield 63%).

EXAMPLE 4

Following the procedure of Example 3 (except that the product was recrystallized from methanol), 8 mmol of the following organic acid chlorides were reacted with 4 mmol of dimethyl 3-oxo-2-(p-chlorophenylhydrazono)glutarate.

1. Isobutyryl chloride reactant gave 600 mg of 6-isopropyl-3,5-bis(methoxycarbonyl)-4-oxo-1-(4-chlorophenyl)-1,4-dihydropyridazine as a yellow solid product, m.p. 203°–205° C.
2. Valeryl chloride reactant gave 700 mg of 6-butyl-3,5-bis(methoxycarbonyl)-4-oxo-1-(4-chlorophenyl)-1,4-dihydropyridazine as a yellow solid product, m.p. 103°–106° C.
3. Benzoyl chloride reactant gave 1.215 g of 6-phenyl-3,5-bis(methoxycarbonyl)-4-oxo-1-(4-chlorophenyl)-1,4-dihydropyridazine as a pale yellow solid product, m.p. 216°–218° C.

EXAMPLE 5

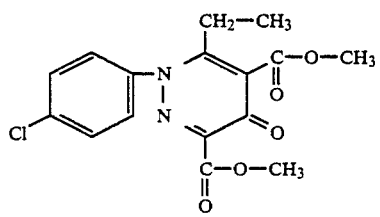

6-ethyl-3,5-bis(methoxycarbonyl)-4-oxo-1-(4-chloro-phenyl)-1,4-dihydropyridazine.

A mixture of 1.25 g (4 mmol) of dimethyl 3-oxo-2-(4-chlorophenylhydrazono)glutarate, 0.404 g (4 mmol) of triethylamine, 1.033 g (4 mmol) of MgBr$_2$ etherate in 15 ml of THF was heated to reflux for about 30 minutes. The mixture was then cooled to about 30° C. and 0.74 g (8 mmol) of propionyl chloride was added with stirring. The mixture was heated to 55° C. and stirred for about ½ hour. The mixture was then cooled to room temperature and mixed with 30 ml of ethyl acetate and 15 ml of 1 N HCl and stirred for 5 minutes. The yield of product was determined by calculating gas chromatograph area percent and was about 75%.

Although this invention has been described with respect to specific embodiments, the details thereof are not to be construed as limitations, for it will be apparent that various embodiments, changes and modifications may be resorted to without departing from the spirit and scope of this invention and it is understood that such embodiments are intended to be included within the scope of this invention.

I claim:

1. A process for making a compound having the formula:

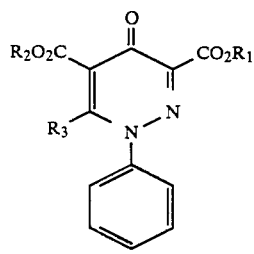

wherein R$_1$ and R$_2$ are each independently a lower alkyl and R$_3$ is a lower alkyl, benzyl or phenyl; which comprises the step of reacting the starting compound having the formula:

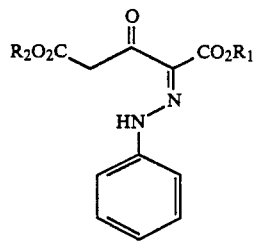

with R$_3$COA wherein A is halo, in the presence of a base and at least about 0.25 molar equivalents of MgX$_2$, wherein X is Cl, Br or I, for each mole of starting compound and the phenyl ring of the starting compound is unsubstituted or substituted with one to three substituents which do not interfere with the process.

2. The process of claim 1 wherein R$_3$ is lower alkyl.

3. The process of claim 2 wherein the process is carried out in the presence of at least about 0.5 to about 1 molar equivalent of MgX$_2$ for each mole of starting compound.

4. The process of claim 3 wherein the base is an alkylamine.

5. The process of claim 4 wherein X is Cl.

6. The process of claim 5 wherein the base is triethylamine.

7. A process for making a compound having the formula:

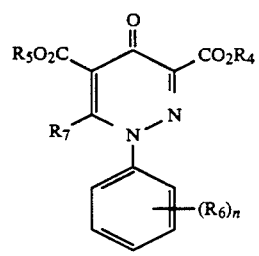

wherein R$_4$ and R$_5$ are each independently a lower alkyl substituent, R$_6$ is a halo substituent; R$_7$ is a lower alkyl substituent and n is 1 to 2; which comprises the step of reacting the starting compound having the formula:

with R$_7$COCl in the presence of a base and at least about 0.25 molar equivalent of MgCl$_2$ for each mole of starting compound.

8. The process of claim 7 wherein the process is carried out in the presence of at least about 0.5 to about 1 molar equivalent of MgCl$_2$ for each mole of starting compound.

9. The process of claim 8 wherein the base is an alkylamine.

10. The process of claim 9 wherein the base is triethylamine.

* * * * *